(12) United States Patent
Linares

(10) Patent No.: US 7,972,380 B2
(45) Date of Patent: Jul. 5, 2011

(54) ARTIFICIAL JOINT SUPPORT BETWEEN FIRST AND SECOND BONES

(75) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 217 days.

(21) Appl. No.: 12/212,161

(22) Filed: Sep. 17, 2008

(65) Prior Publication Data

US 2009/0076605 A1    Mar. 19, 2009

Related U.S. Application Data

(60) Provisional application No. 60/972,909, filed on Sep. 17, 2007.

(51) Int. Cl.
  *A61F 2/08* (2006.01)
  *A61F 2/30* (2006.01)
(52) U.S. Cl. .................. 623/14.12; 623/23.39; 623/23.4
(58) Field of Classification Search .............. 623/16.11, 623/18.11, 19.11–19.4, 20.14–20.15, 20.32–20.33, 623/20.35, 22.11, 22.13, 22.15–22.16, 22.17–22.18, 623/22.21, 22.4, 22.42, 23.11–23.12, 23.39–23.43, 623/17.11–17.4
See application file for complete search history.

(56) References Cited

U.S. PATENT DOCUMENTS

| | | | |
|---|---|---|---|
| 2,667,644 A | 2/1954 | Johnson | |
| 3,306,462 A * | 2/1967 | Da Cruz | 211/49.1 |
| 4,536,898 A * | 8/1985 | Palfray | 623/33 |
| 4,714,477 A | 12/1987 | Fichera et al. | |
| 5,007,934 A | 4/1991 | Stone | |
| 5,047,054 A * | 9/1991 | Vijayan et al. | 623/23.6 |
| 5,092,898 A | 3/1992 | Bekki et al. | |
| 5,171,325 A | 12/1992 | Aulie | |
| 5,263,987 A * | 11/1993 | Shah | 623/18.11 |
| 5,314,478 A * | 5/1994 | Oka et al. | 623/14.12 |
| 5,344,459 A * | 9/1994 | Swartz | 623/14.12 |

(Continued)

FOREIGN PATENT DOCUMENTS

CH    638095 A5 *  9/1983

OTHER PUBLICATIONS

Brown University Division of Engineering. "EN3: Introduction to Engineering and Statics". Oct. 19, 2010 <http://www.engin.brown.edu/courses/en3/Notes/Statics/friction/friction.htm>.*

*Primary Examiner* — David Isabella
*Assistant Examiner* — Andrew Iwamaye
(74) *Attorney, Agent, or Firm* — Gifford, Krass, Sprinkle, Anderson & Citkowski, P.C.

(57) ABSTRACT

An artificial joint associated with an implant including a pair of three dimensional and structurally extending bones, each defining a contoured and opposing end face, and which collectively defines a joint location. At least one plasticized layer is applied to one of, or both, the end faces in a coacting and substantially frictional reducing fashion. A lubricating plastic is defined upon an exposed face of the bladder. The plasticized layers may include a fluid receiving and inflatable bladder for filling a three dimensional area associated with the joint location. A curable/settable fluidic material can be injected into the bladder and which includes at least one of an epoxy, a urethane, a gelatin and a two-part hardener. The bones each further include an artificial implant constructed from at least one of a plasticized and a metallic material.

13 Claims, 9 Drawing Sheets

U.S. PATENT DOCUMENTS

| | | | |
|---|---|---|---|
| 5,389,107 A | 2/1995 | Nassar et al. | |
| 5,545,230 A * | 8/1996 | Kinsinger et al. | 623/38 |
| 5,593,445 A * | 1/1997 | Waits | 623/23.42 |
| 5,676,702 A | 10/1997 | Ratron et al. | |
| 5,728,175 A | 3/1998 | Rincoe | |
| 5,800,566 A | 9/1998 | Gramnas et al. | |
| 5,921,358 A | 7/1999 | Gramnas et al. | |
| 6,627,141 B2 | 9/2003 | McNulty et al. | |
| 6,679,914 B1 * | 1/2004 | Gabbay | 623/14.12 |
| 6,692,679 B1 | 2/2004 | McNulty et al. | |
| 6,800,298 B1 | 10/2004 | Burdick et al. | |
| 6,800,670 B2 | 10/2004 | Shen et al. | |
| 6,818,172 B2 | 11/2004 | King et al. | |
| 7,044,983 B1 | 5/2006 | Cheng et al. | |
| 7,066,958 B2 * | 6/2006 | Ferree | 623/17.12 |
| 7,087,091 B1 | 8/2006 | Chen et al. | |
| 7,109,181 B2 | 9/2006 | Cowlen et al. | |
| 7,148,209 B2 | 12/2006 | Hoemann et al. | |
| 7,175,666 B2 | 2/2007 | Yao | |
| 7,179,298 B2 | 2/2007 | Greenlee | |
| 7,186,364 B2 | 3/2007 | King et al. | |
| 7,331,995 B2 | 2/2008 | Eisermann et al. | |
| 7,338,532 B2 * | 3/2008 | Haberman et al. | 623/38 |
| 7,384,430 B2 | 6/2008 | Greer et al. | |
| 7,563,285 B2 * | 7/2009 | Ralph et al. | 623/17.14 |
| 7,758,643 B2 * | 7/2010 | Stone et al. | 623/14.12 |
| 7,857,854 B2 * | 12/2010 | Sweeney | 623/17.11 |
| 2003/0036797 A1 * | 2/2003 | Malaviya et al. | 623/14.12 |
| 2003/0093152 A1 * | 5/2003 | Pedersen et al. | 623/14.12 |
| 2003/0171812 A1 * | 9/2003 | Grunberg et al. | 623/17.11 |
| 2004/0024460 A1 | 2/2004 | Ferree | |
| 2004/0068322 A1 | 4/2004 | Ferree | |
| 2004/0260396 A1 * | 12/2004 | Ferree et al. | 623/17.12 |
| 2005/0192674 A1 | 9/2005 | Ferree | |
| 2006/0009850 A1 * | 1/2006 | Frigg et al. | 623/17.13 |
| 2007/0050036 A1 * | 3/2007 | Felt et al. | 623/14.12 |
| 2007/0106391 A1 * | 5/2007 | Ronk | 623/22.21 |
| 2007/0282443 A1 * | 12/2007 | Globerman et al. | 623/17.11 |
| 2008/0161919 A1 * | 7/2008 | Melkent | 623/17.11 |
| 2008/0183296 A1 * | 7/2008 | Ferree | 623/17.16 |
| 2008/0234827 A1 * | 9/2008 | Schaller et al. | 623/17.16 |
| 2009/0118836 A1 * | 5/2009 | Cordaro | 623/17.16 |
| 2010/0070042 A1 * | 3/2010 | Bryan et al. | 623/17.16 |
| 2010/0106252 A1 * | 4/2010 | Kohm et al. | 623/17.16 |
| 2011/0066192 A1 * | 3/2011 | Frasier et al. | 606/86 A |

* cited by examiner

US 7,972,380 B2

ARTIFICIAL JOINT SUPPORT BETWEEN FIRST AND SECOND BONES

CROSS-REFERENCE TO RELATED APPLICATIONS

This Application is a Non-Prov of Prov (35 USC 119(e)) application 60/972,909 filed on Sep. 17, 2007 for an Artificial Knee Implant Including Liquid Ballast Supporting Rotating/Translating Surfaces, and Overlapping Disk Variants.

FIELD OF THE INVENTION

The present invention is an artificial implant for use with either real or artificial human bones. In particular, the implant of the present invention is an improvement over prior art implants, typically those constructed of a metallic or other synthetic material, in that it provides ballasting and frictionless support to opposing ends of first and second bones associated with such as a knee joint. In addition to providing support through the injection of ballasting fluid into a bladder defined between the bones, the present invention further provides a wide variety of additional structures for more effectively establishing cushioning and multi-directional support in the artificial joint area.

BACKGROUND OF THE INVENTION

The prior art is well documented with examples of artificial (or prosthetic) implant joints and related assemblies, the purpose for which being to replace an existing joint which has become worn through extended wear or irreplaceably damaged through disease or injury. One objective of such artificial joint implants, whether adapted for use with an existing bone remaining in the patient or as a component of one or more skeletal implants which includes a built-in joint, is in providing a desired amount of cushioning support. Examples of existing implant assemblies with built-in dampening means include, among others, the modular implant with micro-motion damper as set forth in U.S. Pat. No. 7,156,666, to Yao and the shock absorbent prosthetic hip joint of Nasser, U.S. Pat. No. 5,389,107.

SUMMARY OF THE INVENTION

The present invention discloses an artificial joint associated with an implant including a pair of three dimensional and structurally extending bones, each defining a contoured and opposing end face, and which collectively defines a joint location. At least one plasticized layer is applied to one of, or both, the end faces in a coacting and substantially frictional reducing fashion. A lubricating plastic is defined upon an exposed face of the bladder.

The plasticized layers may include a fluid receiving and inflatable bladder for filling a three dimensional area associated with the joint location. A curable/settable fluidic material can be injected into the bladder and which includes at least one of an epoxy, a urethane, a gelatin and a two-part hardener. The bones each further include an artificial implant constructed from at least one of a plasticized and a metallic material, with the bones each having a specified shape and size and establishing a joint selected from a group including at least one of upper/lower knee joint and an outer/inner ball and socket joint.

In another application, a plurality of overlapping disk elements are secured to a selected joint defining end face, and in order to permit a range of multi-directional and frictionless motion of an opposing bone end face. In a further subset application, a plurality of concentrically defined, and independently rotatable, elements are secured to a selected joint defining end face. A plurality of radially directed and lubricating passageways can further be defined in the individual elements.

Other applications include a plurality of at least one of individual plasticized rollers and roller supported belts for providing substantially frictionless and movable motion between the joint defining bones. To reinforce the implant assembly, an inner reinforcing member can be inserted, within an existing outer bone, and surrounded by a volume of the injectable and settable ballasting fluid. The plasticized layer may further have a specified shape and size and further includes an antimicrobial plastic.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

Figure 1:
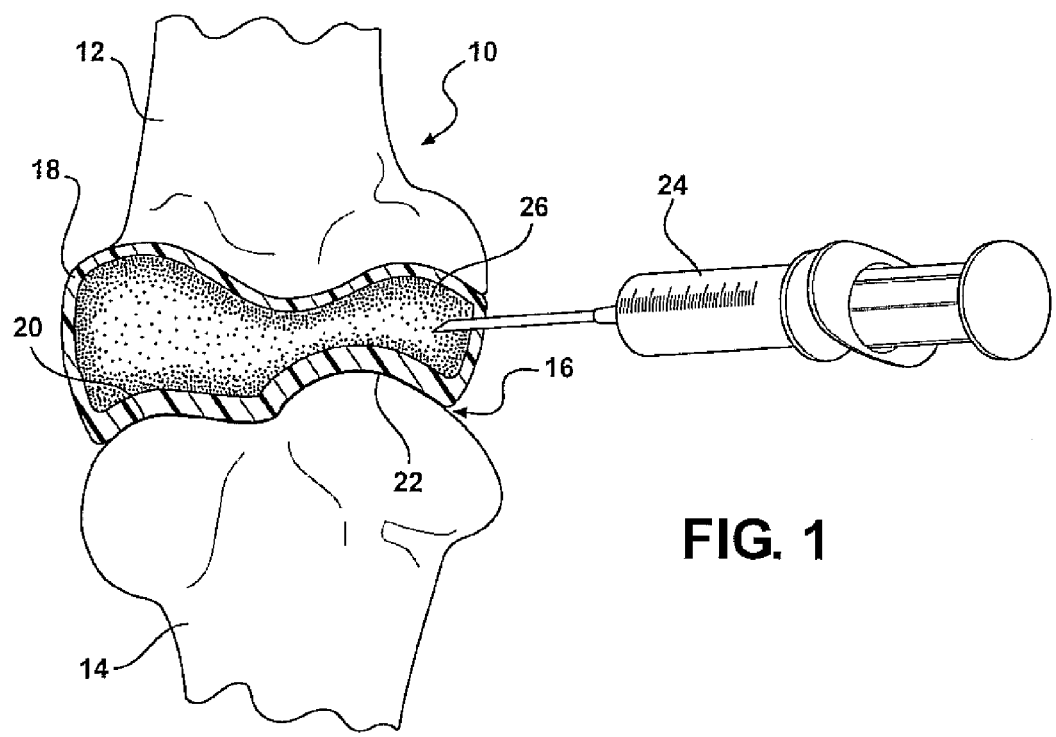
FIG. 1 is an illustration of an artificial knee implant according to a preferred embodiment of the present invention and exhibiting first and second bones, between which are disposed a ballasting bladder (such as secured to an end of a first bone) and further including an opposing and mating lubricating plastic for establishing effortless contact with a second of the bones.

Referring now to FIG. 1, a first embodiment is illustrated at 10 of an artificial knee/joint implant according to the present inventions. As previously described, the skeletal implant is intended to operate as a replacement for human bone and joint structure (such as resulting from disease, accidents, etc.) and which is further an improvement over existing prosthetic metal implants and the like in that it provides improved support between the end faces of the bones defining the joint application.

The knee and ligament embodiment featured at 10 exhibits first 12 and second 14 bones, these typically corresponding to a patient's upper and lower leg bones, and which further define particularly configured and opposing/seating locations, these further being generally defined by a joint region 16. As further understood, the bones 12 and 14 are typically provided as artificial prostheses, these including such as plastic, metal or other suitable material constructions which exhibit the necessary properties of durability and resilience. It is also envisioned that the bones 12 and 14 can be of a natural construction, and can further include those native to the patient within which the artificial joint assembly is being installed.

An inflatable and ballasting bladder 18, this being defined by such as a fluid retaining and flexible/stretchable body constructed of a plasticized or other suitable artificial material, is provided and can be thermoformed, or otherwise applied upon an opposing end surface of a selected bone (in this instance upper bone 12). An exposed surface of the bladder 18 is coated with a lubricating (e.g. typically sanitary) plastic layer, at 20, this in turn establishing a substantially frictionless/effortless contact with an opposing surface 22 associated with the second 14 of the artificial bones. Although not further shown in either this or the succeeding embodiments, it is further understood that a suitable ligament structure is employed for retaining the bones and resultant joint created therebetween in a desired relative positioning.

A needle 24 (or other suitable fluid injection mechanism) is provided for injecting a specified volume of a ballasting fluid 26 (this including such as water based or other synthetically derived fluid based composition) and which operates to ballast the joint region 16 to a desired pressure/configuration. In a preferred variant, the injected ballast, upon injection, conforms to the contour/shape of the joint (in particular to fill the gaps/spaces between the bones), and further concurrent with setting/hardening of the fluid. In this fashion, a combination durable, form-fitting, cushioning and substantially frictionless surface is created in the defined knee joint area 16 between the bones 12 and 14.

Figure 2:
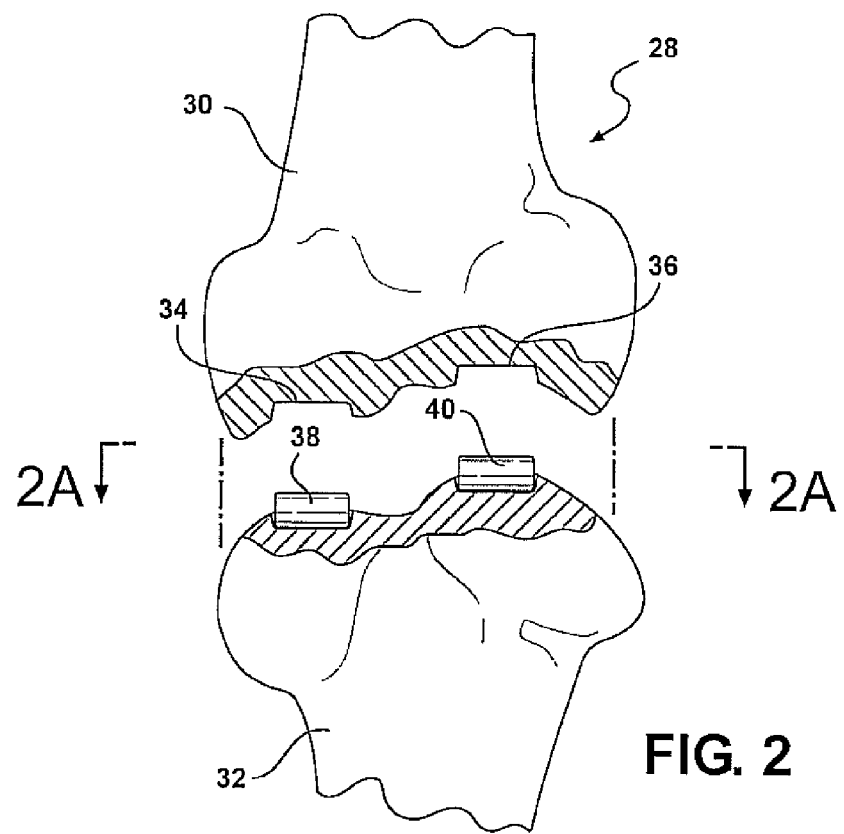
FIG. 2 is an illustration of an alternate variant of artificial knee implant and which utilizes a plurality of overlapping and freely inter-slidable roller portions in substitution for the fluid ballasting bladder.

Referring now to FIG. 2, an illustration is shown at 28 of an alternate variant of artificial knee implant, again exhibiting first 30 and second 32 bones (e.g. such as metal/plastic artificial bones). The first of the bones 30 exhibits an end surface defined, in relevant part, by a pair of generally linear and spaced apart channels (or tracks) 34 and 36. The other, in this case lower-disposed, bone 32 exhibits an opposing joint defining end surface and which utilizes a plurality of overlapping and freely inter-slidable roller portions, see at 38 and 40, and which are provided in substitution for the fluid ballasting bladder 18 illustrated in FIG. 1.

Figure 2A:
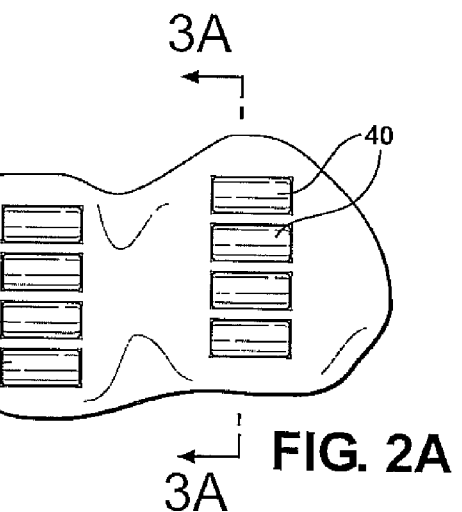
FIG. 2A is an end view of a male bone and illustrating first and second individual pluralities of rollers encased with a plastic/Teflon material.
Figure 3A:
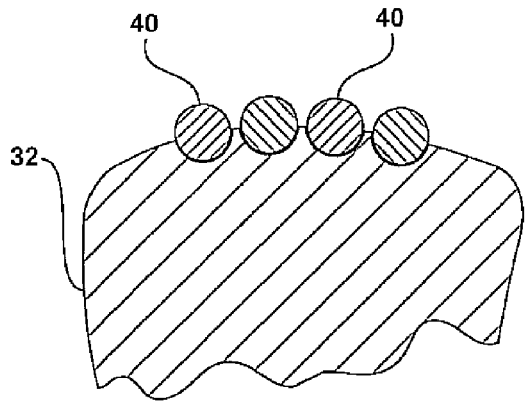
FIG. 3A is an end cutaway view taken along line 3A-3A of FIG. 2A and illustrating the multiple roller configuration associated with the joint configuration.

FIG. 2A illustrates an end view of a male bone, with the first and second individual pluralities of rollers 38 and 40 being encased with a plastic/Teflon material and in turn seated upon the end face of the bone 32 in aligning and opposing fashion relative to the channels/tracks 24 and 26. The individual sets of rollers may further exhibit varying configurations (see plurality of three rollers 38 and separate plurality of four rollers 40 in the end view illustration of FIG. 2A) and, as will be described in additional detail with reference to succeeding variants, can further exhibiting other multi-directional displacement characteristics. FIG. 3A is a cutaway view taken along line 3A-3B of FIG. 2A and illustrating the multiple roller configuration associated with the joint configuration. Although not clearly illustrated, it is understood that a suitable pin axis can be incorporated for mounting each of the rollers in rotating fashion, such anchoring a midpoint side location of each roller to the surface of the bone end to prevent displacement or dislodgment of the roller from its seating/contacting locations relative to the opposing end faces.

Figure 2B:
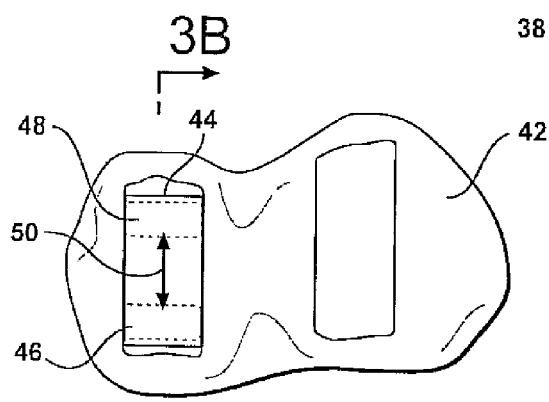
FIG. 2B is an end view of a further configured male bone and illustrating a single pair of cushioning and elongated belt supports.
Figure 3B:
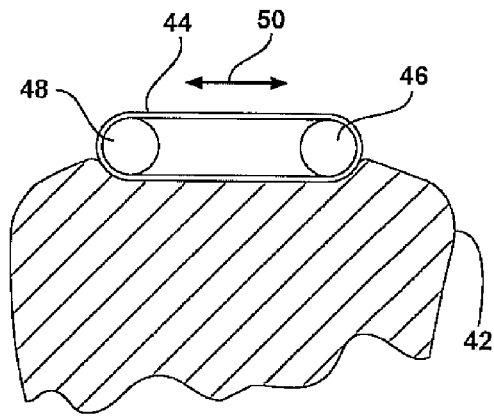
FIG. 3B is an end cutaway view taken along line 3B-3B of FIG. 2B and illustrating the selected elongated belt support associated with that selected joint configuration.

Referring to FIG. 2B (as well as end cutaway in FIG. 3B), an end view is shown at of a further configured male bone 42 and illustrating a single pair of cushioning and elongated belt supports, see at 44. The belt supports 44 are further shown in cutaway along line 3B-3B of FIG. 2B (see also FIG. 3B), and which illustrates the selected elongated belt 44 supported on a pair of rollers 46 and 48, these associated with that selected joint configuration. Unlike the ballasting bladder and lubricated plastic covering associated with certain of the previous embodiments, the belt support 44 provides bi-directional support, see arrow 50.

The belt support 44 can be constructed from a similarly lubricating plastic and similarly frictionless material and, when viewing the illustrations of FIGS. 1 and 2, it is understood that the belt supports can be located on opposing end faces of either the upper or lower artificial bones, as well as capable of being translated in additional directions through contact with an opposing joint defining bone end face. As previously described, the rollers 46 and 48 may each include a suitable mounting pin or the like for securing in place in exposed (and partially projecting) fashion relative to the opposing and contacting bone end, and joint defining, face.

Figure 2C:
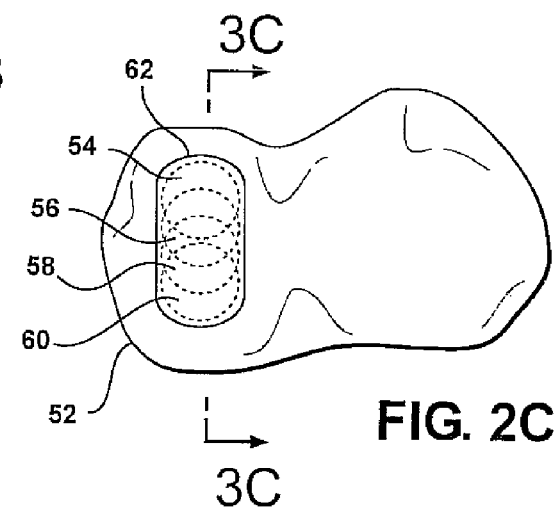
FIG. 2C is an end view of a still further variant of male knee bone and illustrating a first configuration of overlapping disks associated with multi-directional cushioning support of an opposing bone.
Figure 3C:
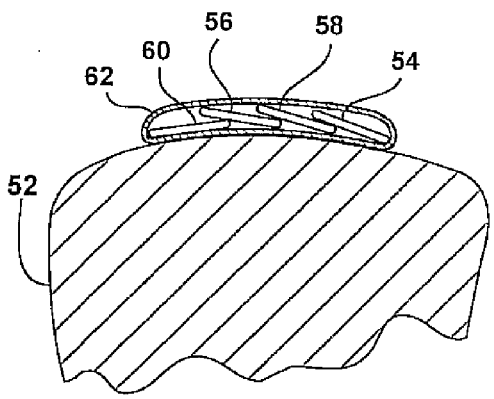
FIG. 3C is an end cutaway view taken along line 3C-3C of FIG. 2C and illustrating the overlapping disk arrangement.

FIG. 2C, in cooperation with associated end cutaway of FIG. 3C, is an end view of a still further variant of male knee bone 52 and illustrating a first configuration of overlapping disks 54, 56, 58, 60, et. seq., associated with multi-directional cushioning support of an opposing bone. In particular, the plurality of disks 54-60 illustrated in the rotated sectional view taken from FIG. 2c, are constructed of a likewise lubricated, sanitary and substantially frictionless plasticized material and operate to provide a limited degree of multi-directional movement when contacted by an opposite joint defining bone end face.

As further shown in FIG. 2C sectional cutaway inset, the disks 54-60 can be shaped in a slightly arcuate profile, this accounting for the bone to bone end face configuration associated with the region in which the overlapping/sliding disks are located. The disks may further be secured in place, such as by a flexible and translatable covering material as representatively shown at 62 in FIG. 2C. Alternatively, the disks may be seated or otherwise secured together in another fashion and further such that they maintain an integrated and effective movement-permitting joint surface.

Figure 2D:
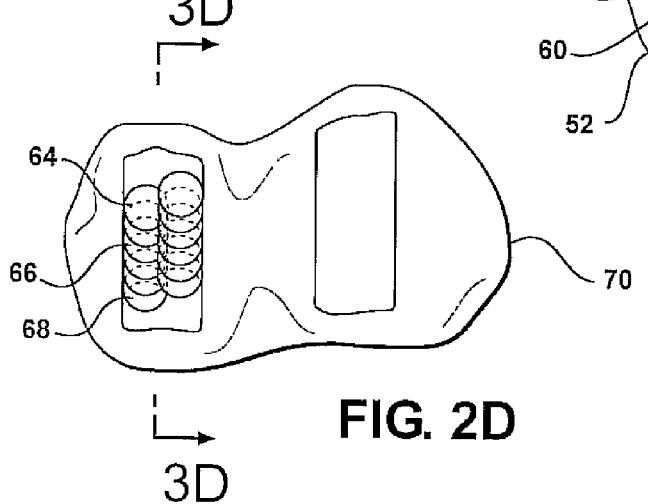
FIG. 2D is similar to FIG. 2C, but presents a further possible configuration of a greater plurality of smaller sized and overlapping disks associated with a knee bone supporting location.
Figure 3D:
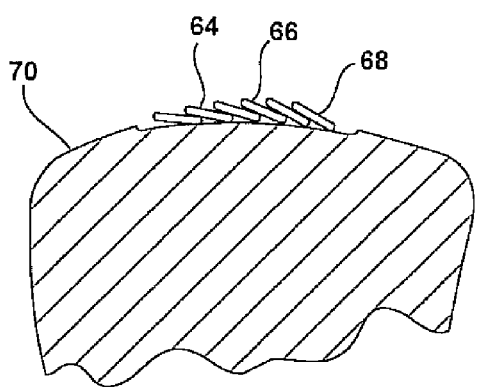
FIG. 3D is an end cutaway view taken along line 3D-3D of FIG. 2D and illustrating the modified overlapping disk arrangement.

FIG. 2D is an illustration similar to FIG. 2C, but presents a further possible configuration of a greater plurality of smaller sized and overlapping disks, one plurality of which is shown at 64, 66, 68, et. seq. associated with a knee bone supporting location 70. The arrangement of FIG. 2D is otherwise largely similar to that shown in FIG. 2C, with the exception that increasing the number of disks (as well as decreasing the size of each disk) has a resultant effect on the permissive range of multi-directional and frictionless motion of the joint in multiple defined directions. The arrangement of FIG. 3D may or may not include a covering or restraining material (such as shown at 62 in FIG. 3C) for maintaining the disks in place, as well as for permitting the necessary range of motion to the joint assembly. Reference is also made to the end cutaway view of FIG. 3D and which illustrates the smaller size of the overlapping disks relative to that shown in FIG. 3C.

Figure 4:
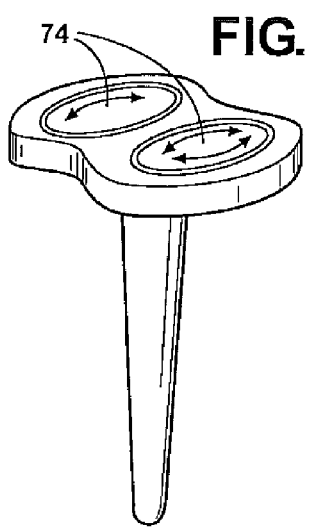
FIGS. 4, 4A and 4B illustrate three potential variations of multi-directional end-face joint supports, including linear, semi-linear and fully rotatable support surfaces.
Figure 4A:
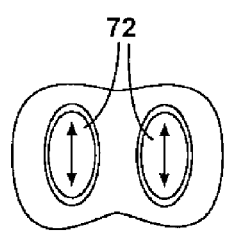
Figure 4B:
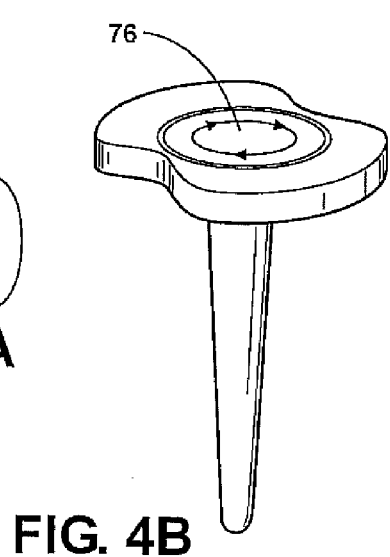

FIGS. 4, 4A and 4B illustrate three potential variations of multi-directional end-face joint supports and by which such combined displaceable/rotational motion is built into a joint defining implant component. These include a pair of linear supporting (and selectively displaceable) surfaces, see pair of side-by-side located surfaces at 72 in FIG. 4A, as well as semi-linear/semi-rotatable surfaces, at 74 in FIG. 4, and fully rotatable support surfaces, at 76 in FIG. 4A. The alternate configurations in FIGS. 4-4B are intended to illustrate what possible variations are available for joint defining and movable support surfaces incorporated into such artificial implants and joints, and by which varying degrees of displaceable (combined linear and rotatable) support is achieved along a specified and opposing joint defining face.

Figure 5:
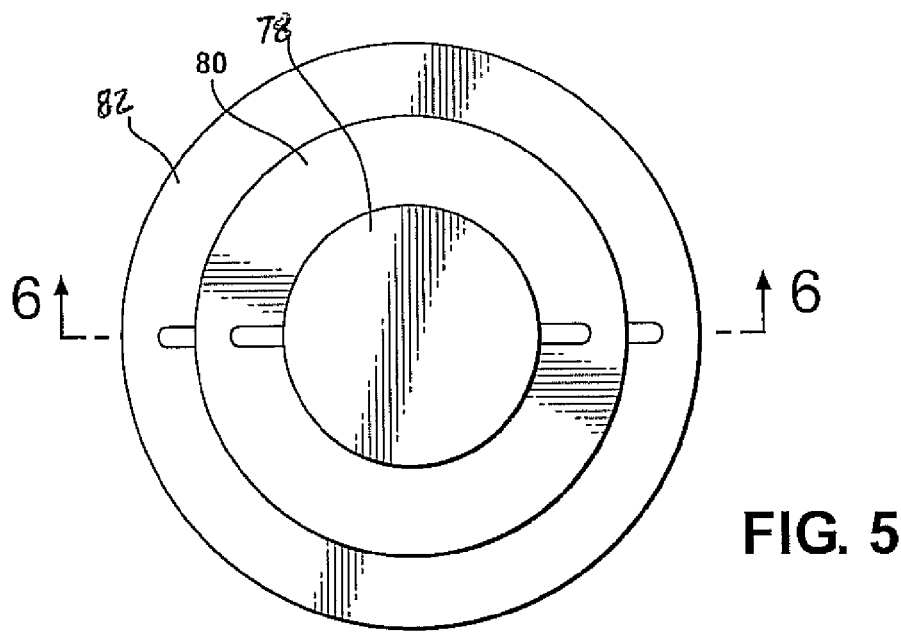
FIG. 5 is an end-face illustration of a plurality of overlapping and varying diameter sized disks for permitting eccentric joint supporting travel.

Referring now to FIG. 5, an end-face illustration is shown of a plurality of overlapping and varying diameter sized disks, see outer disk 78, intermediate disk 80 and inner disk 82 for permitting eccentric joint supporting travel between opposing and joint defining bones (not shown). As further shown in FIG. 6, a cutaway taken along line 6-6 of FIG. 5 better illustrates the seating of underside tabs, see further as respectively shown at 84, 86 and 88 for disks 78-82, associated with each disk. Each tab seats within an underlying defined channel in a succeeding (underlying) disk, and in order to establish a range of controlled eccentric motion of the joint created by the collective multiple sandwiching disks.

Figure 6:
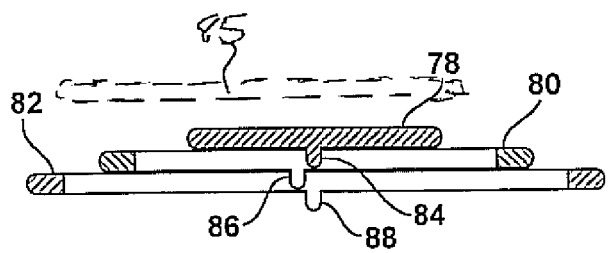
FIG. 6 is a cutaway taken along line 6-6 of FIG. 5 and better showing the seating of underside tabs associated with each disk within an underlying defined channel in a succeeding disk, and in order to establish controlled eccentric motion of the joint created by the multiple sandwiching disks.

As shown in FIG. 6, a support surface 85 can define either an opposing and joint defining bone surface or, alternatively, a veneer/retaining surface intended to retain the overlapping and movable disks in place, and while permitting their limited lateral movement while concurrently preventing the disks from becoming disassembled. In use, the disks will allow for eccentric travel in all two dimensional directions.

Figure 7:
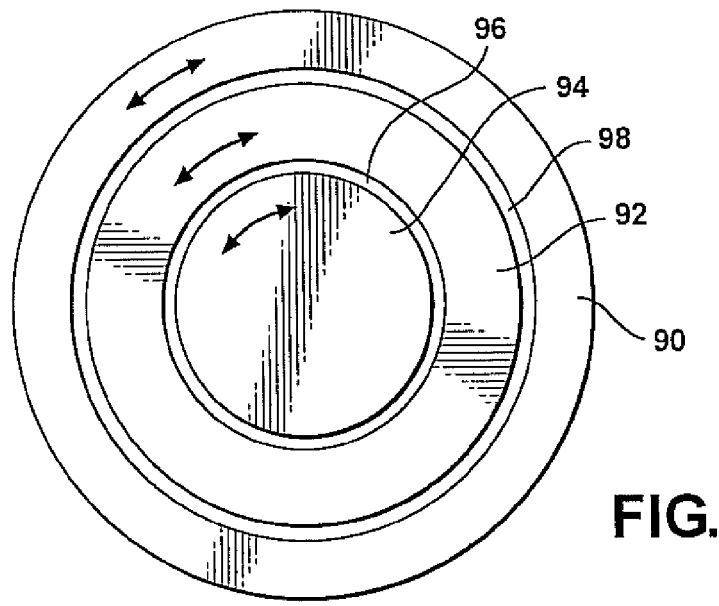
FIG. 7 is an end view of a still further joint configuration and showing concentric and opposing rotatable ring portions.

FIG. 7 is an end view of a still further joint configuration and showing concentric and opposing rotatable disk/ring portions 90, 92 and 94. The arrangement of FIG. 7 is intended in conditions where multiple-eccentric motion of a user's (knee) joint is such that it would be advantageous to have multi-directional capabilities built into the joint and such as is defined by the alternating counter clockwise outer-most ring 90, intermediate clockwise ring 92 and, again, counter clockwise rotational and inner-most disk 94 in rotative displacement with the outer concentric rings. Ring-shaped supporting surfaces, see at 96 and 98, can be provided and which allow the inner-most ring 94 and outer concentric disks 90 and 92 to individually rotate in their desired directions, and without significant frictional resistance between adjoining disks. The rings 90, 92 and 94 are constructed in such a fashion to define a joint end face which provides coaxial and multi-rotational displacement.

Figure 8:
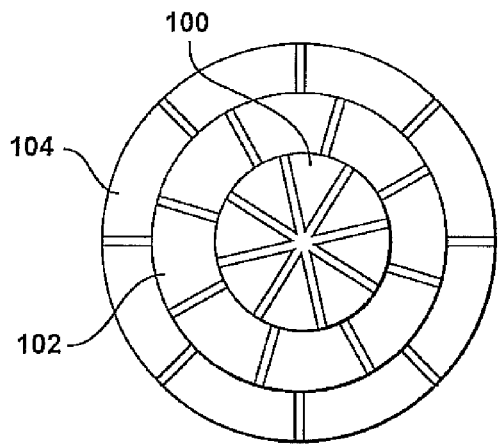
FIG. 8 is an end view of a yet further version of a joint arrangement and one which illustrates pluralities of individual and radially communicating lubricating passageways associated with a modification of each of the plurality of disks, such as also shown in FIG. 5.
Figure 8A:
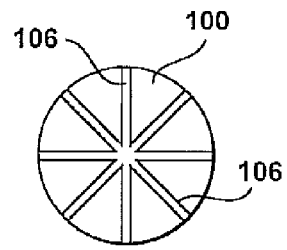
FIGS. 8A-8C are respective illustrations of the inner-most, middle and outermost disks in FIG. 8, and depicting likewise offset lubricating patterns.
Figure 8B:
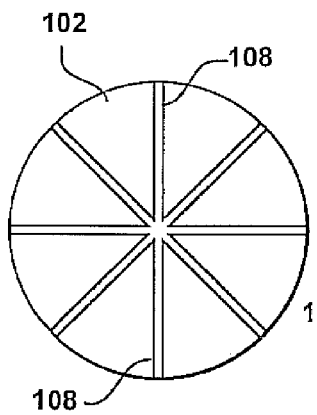
Figure 8C:
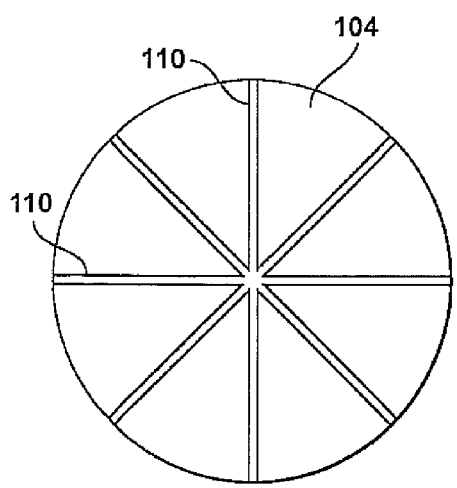

FIG. 8 is an end view of a yet further version of a joint arrangement, and one which illustrates pluralities of individual and radially communicating lubricating passageways associated with a modification of each of the plurality of disks, such as also shown in FIG. 5. As also shown in FIGS. 8A-8C, respective illustrations are presented of inner-most 100, middle 102 and outermost 104 disks assembled together in FIG. 8, these likewise depicting (both individually and upon assembly together) offset and radially projecting lubricating patterns, at 106, 108 and 110, respectively.

Although not clearly shown, it is understood that the overlapping disks are assembled in such a fashion that each of the disks 100 and 102 are both capable moving eccentrically relative to the outermost (and optionally fixed) disk 104. The various disks are further assembled in a fashion which prevents the disks 100 and 102 from becoming detached from the outermost disk 104, this potentially including the provision of underside seating tabs or other suitable structure for both providing inter-relating and restricted motion along the bottom or sides of the overlapping disks.

Figure 9:
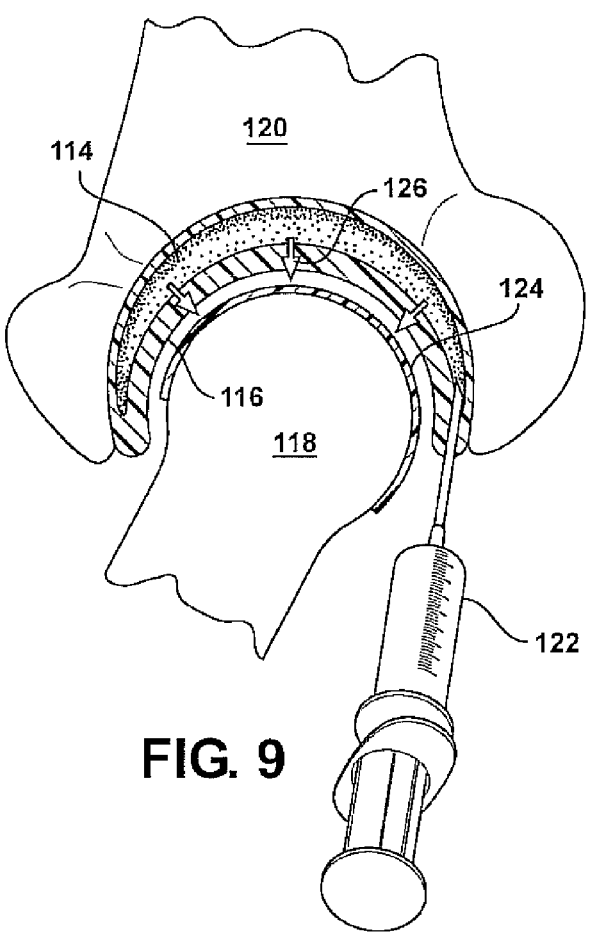
FIG. 9 is an illustration of a socket type arrangement for a cushioning joint and which exhibits a generally annular and bowl-shaped fluid ballasting bladder and adjoining lubricating plastic layer disposed between inner ball and outer socket portions of a joint.

Proceeding to FIG. 9, an illustration is shown of a socket type arrangement for a cushioning joint, see generally at 112, and which exhibits a generally annular and bowl-shaped fluid ballasting bladder 114 and adjoining lubricating plastic layer 116 disposed between an inner ball 118 and outer socket 120 portion of an annularly defined joint. The ball and joint are defined again by such as plastic or other suitable high durability/impact resistant bone implants, and a needle or other injection medium is again shown, at 122, for ballasting the bladder 114 through the insertion of fluidized medium. The fluid can again include such as a epoxy/urethane/gelatin and which may also incorporate a two part hardener in order to cure and harden the mixture upon insertion and upon formation of the bladder to the desired supporting shape. As also shown, the inner ball 118 can also include an outer annular/curved lubricated plastic layer 124, this slidably contacting the opposing layer 116 formed upon the expandable/ballasting bladder 114, and upon the bladder being inflated as indicated by reference arrows 126.

Figure 10:
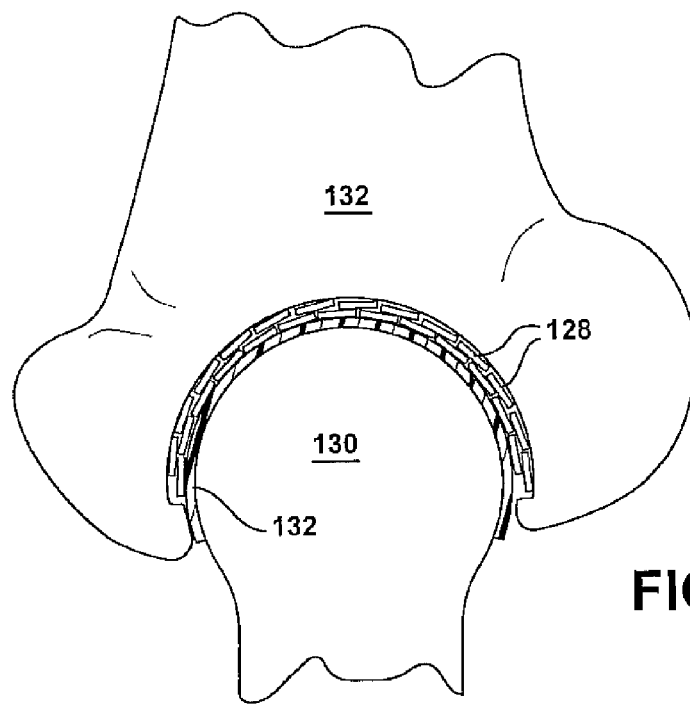
FIG. 10 is an illustration of a further variation of socket joint and including a plurality of overlapping disk elements arranged in a generally curved/arcuate pattern.

FIG. 10 is an illustration of a further variation of socket joint and including a plurality of overlapping disk elements 128 arranged in a generally curved/arcuate pattern between a modified inner ball 130 and outer socket 132. While illustrated with an exaggerated clearance, it is understood that the disk elements 128 substitute for the ballasting/inflatable bladder shown in FIG. 9, and further that a lubricated plastic layer 132 (similar to that also shown at 124 in FIG. 9) is provided contacts the sanitary plastic and frictionlessly displaceable disks 128.

Figure 10A:
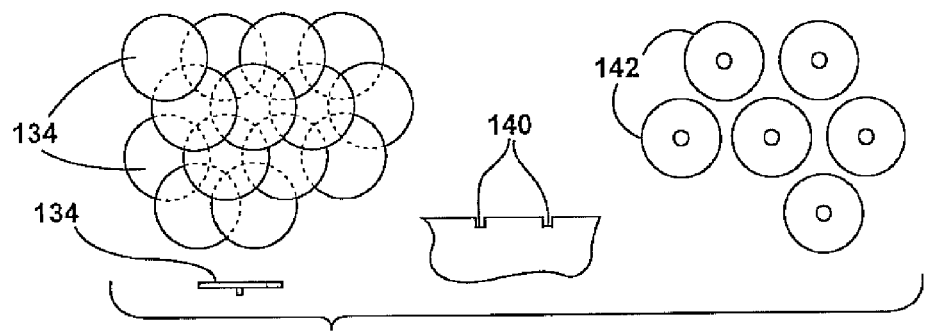
FIG. 10A is a collection of potential disk configurations which can be incorporated into the socket arrangement of FIG. 10.
Figure 10B:
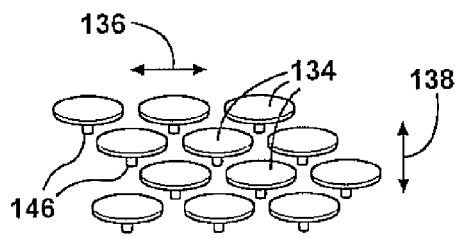
FIG. 10B is a sectional illustration of the disk elements arranged in the embodiment of FIG. 10.

FIGS. 10A and 10B each further illustrate, at 134, a collection of potential disk configurations which can be incorporated into the socket arrangement of FIG. 10. In particular, the disks are provided with underside projecting tab or stem portions (see at 146 in FIG. 10C), similar to that referenced in preceding illustrations, and which allows limited movement in both of first 136 and second 138 axial directions (see further again FIG. 10B).

As again shown in FIG. 10A, seating surfaces associated with the joint may include receiving slots or apertures, see at 140, within which the stem portions 146 of associated disks 134 are supported and the disks allowed to displace in their limited lateral and height defining dimensions. The plural and overlapping relationship between the disks 134 is further such that they may be relatively easily retained in place within the defined joint.

Figure 10C:
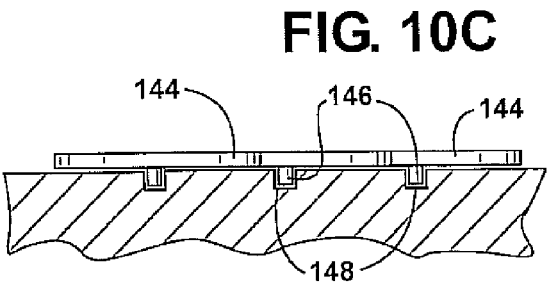
FIG. 10C is a further configuration showing a plurality of disks with underside projecting tabs arranged in a limited multi-directional displacement relative to a bone surface upon which the disks are seated.

Referring again to the subset illustration in FIG. 10A, further collection of ring shaped locations are further referenced at 142, these associated with the apertures 140 illustrated and further such that the pair of apertures 140 shown can also define a circular seating channel associated with a given selected ring location 142. FIG. 10C is a her configuration showing a plurality of disks 144, again with underside projecting tabs 146 arranged in a limited multi-directional displacement relative to a bone surface with plural seating recesses, 148, upon which the disks are seated.

Figure 11:
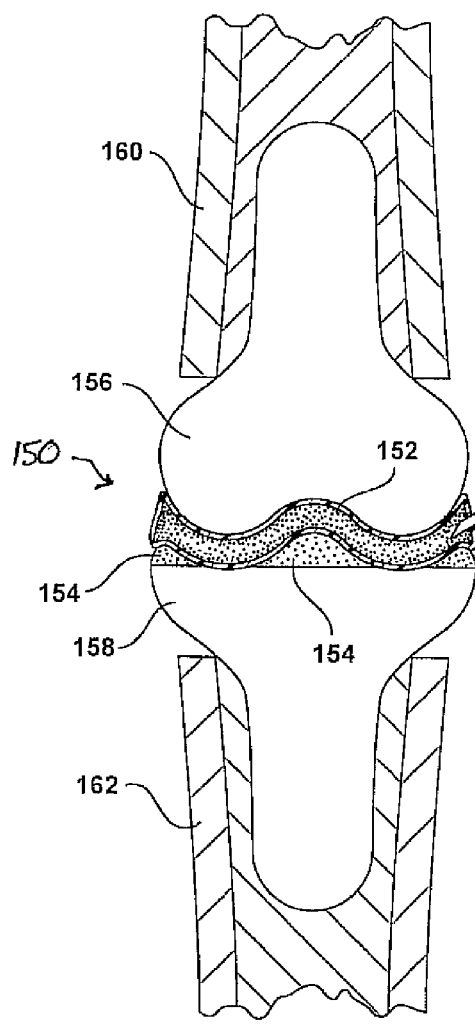
FIG. 11 is an illustration of a retrofit application of a pre-existing artificial joint, and which includes both new lubricant plastic layer and ballasting bladder.

FIG. 11 is an illustration at 150 of a retrofit application of a pre-existing installed artificial joint, and which includes both a new lubricant plastic layer and combination ballasting bladder 152, and which is overlayed over a pre-existing plasticized (substrate) layer 154. End most located bones 156 (male) and 158 (female) are typically constructed of metal, this being typical of the recent area marking the advances in artificial and prosthetic implants. Supporting ligaments, not shown, are provided for securing the end most located bones 156 and 158, these in turn being encased and supported by skeletal supporting bones 160 and 162 for positioning and maintaining the joint defined between the bones 156 and 158. An annular outer seal, see at 160, maintains the structural integrity of the joint and prevents either the lateral bulging displacement of the inflatable ballasting layer and/or the escape of fluid prior to the same curing and hardening with the three dimensionally defined joint. An injection needle is again shown at 122 and which can inject a desired volume of fluid within the bladder 152.

Figure 11A:
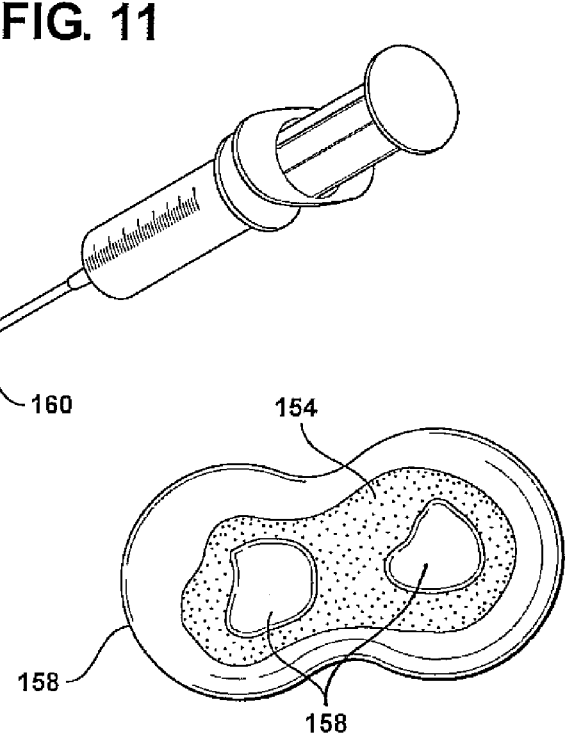
FIG. 11A is an end view of a pre-existing artificial (metal and plastic) bone shown in FIG. 11, and prior to application of a retrofit joint.
Figure 11B:
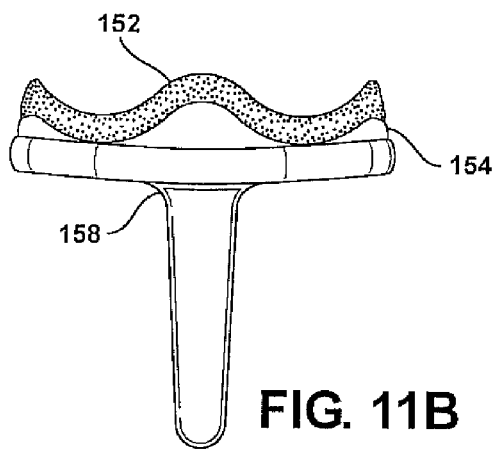
FIG. 11B is a rotated side view of artificial bone shown in FIG. 11A and further illustrating the new layer of a lubricant plastic applied according to a selected retrofit step.
Figure 11C:
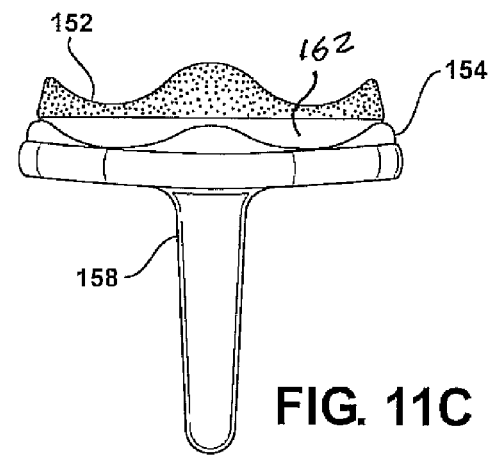
FIG. 11C is an alternate variant to that shown in FIG. 11B and by which a volume of a glue is inserted between an old plastic layer and a retrofit lubricant plastic.

FIG. 11A is an end view of a selected pre-existing artificial (metal and plastic) bone 158 shown in FIG. 11, and prior to application of the retrofit joint described. FIG. 11B is another and rotated side view of the artificial bone 158 shown in FIG. 11A, and further illustrating the new layer of a lubricant plastic 152 applied according to a selected retrofit step. Proceeding to FIG. 11C, an alternate variant to that shown in FIG. 11B is referenced and by which a volume of a glue 162 is inserted between the old plastic layer 154 and newly/applied retrofit lubricant plastic 152. Additional options associated with the present design is the creation of a very small/fine incision in the region associated with the joint retrofit, and without the requirement of having to previously remove or otherwise tamper with the previously installed implant/prosthetics.

Figure 12:
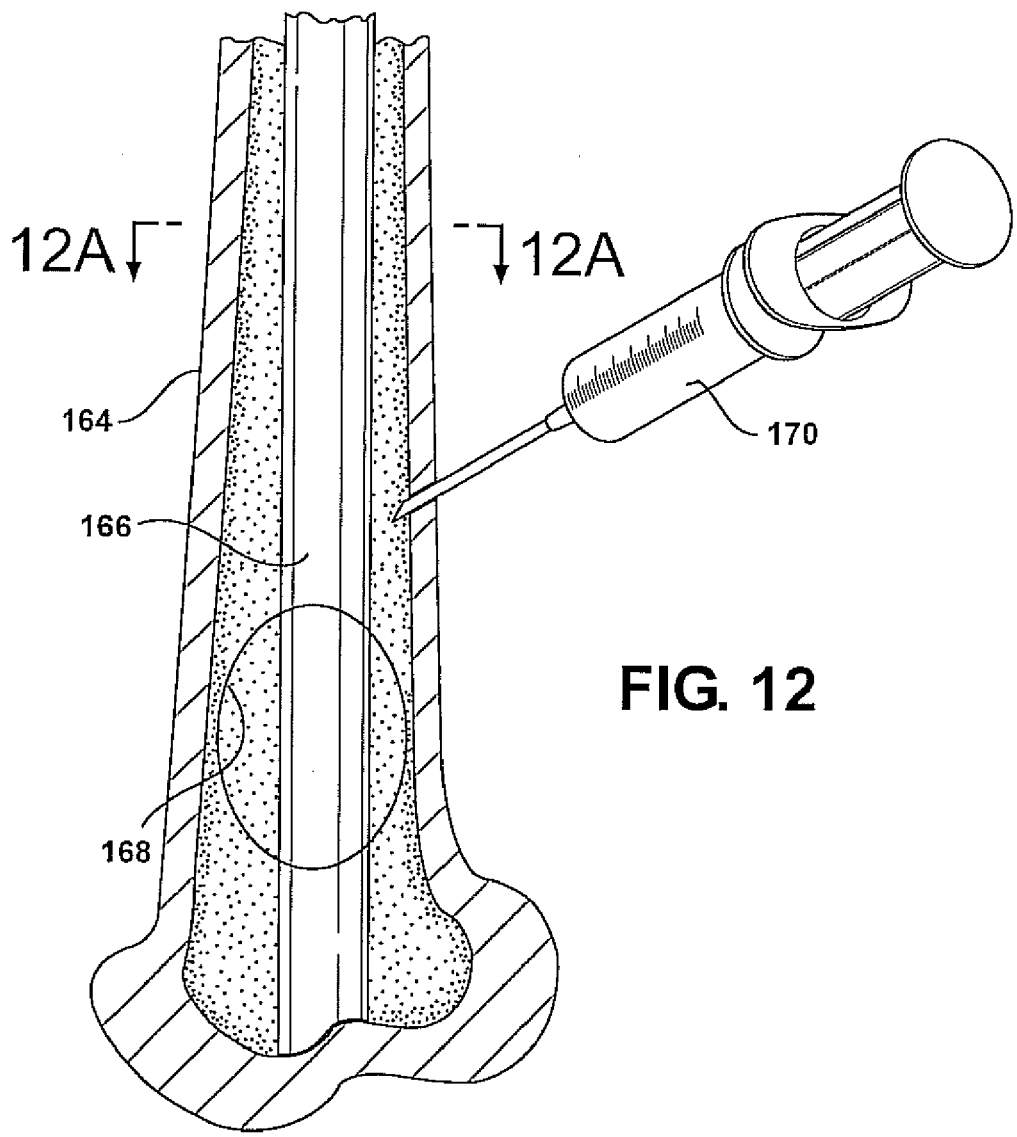
FIG. 12 is an illustration of an existing bone, within which an internal support plastic support is installed.
Figure 12A:
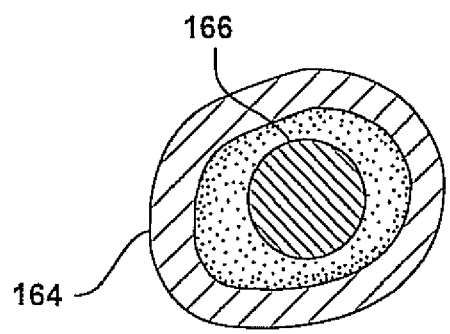
FIG. 12A is a cutaway view taken along line 12A-12A of FIG. 12 and showing the concentric nature of the outer existing bone and inner disposed plastic support.

Referring now to FIG. 12, an illustration is shown at 164 of an existing bone according to a yet further preferred variant, and within which an internal support plastic support 166 is installed to provide the bone with additional structural rigidity. In this application, a hole/circular incision is defined, see at 168, at a suitable location within the surface structure of the bone 164. The insert support, previously illustrated at 166, is inserted lengthwise and until it fully seats into the substantially hollow bone interior (as shown in cutaway). At this point, a volume of injected fluid, see at 170, is filled into the surrounding space defined between the exterior surfaces of the plasticized insert and the interior walls of the bone. FIG. 12A is a cutaway view taken along line 12A-12A of FIG. 12 and showing the concentric nature of the outer existing bone 164 and inner disposed plastic support 166

Figure 13:
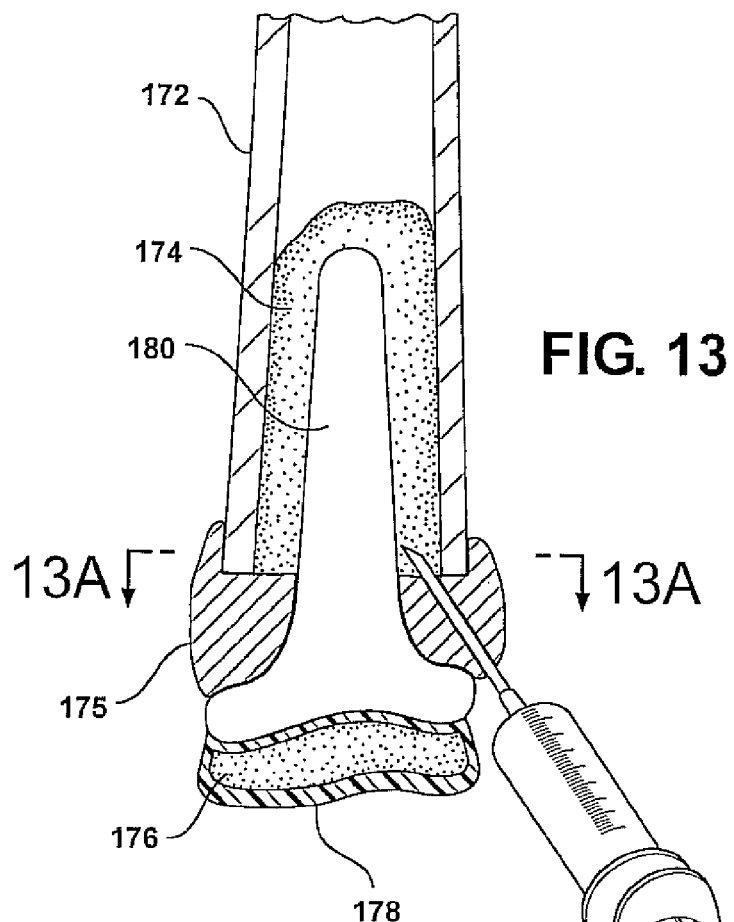
FIG. 13 is a cutaway illustration of a further ballasting arrangement of a combination bone and joint and showing a shape following internal inflatable bladder and in combination with a secondary end joint defining bladder exhibiting an external lubricant plastic face.
Figure 13A:
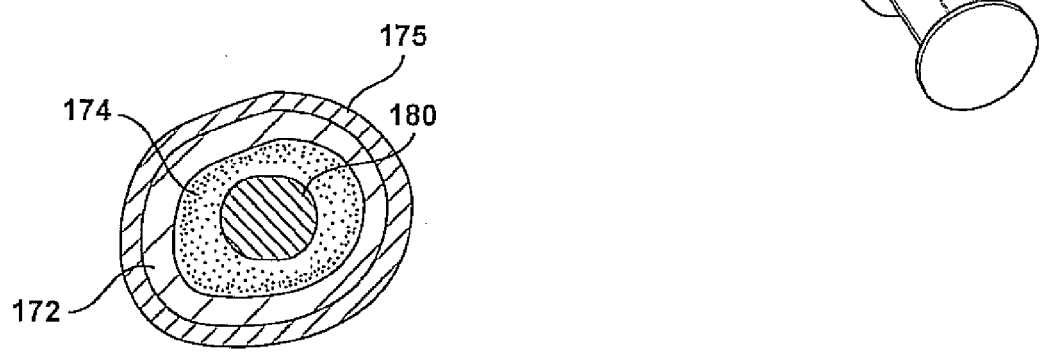
FIG. 13A is a cutaway view taken along line 13A-13A of FIG. 13 and showing the concentric arrangement of the inner plastic support, injected liquid plastic bladder, and outer bone.

Finally, and referring to FIG. 13, a cutaway illustration is shown of a further ballasting arrangement of a combination bone 172 and joint, and showing a shape following internal inflatable bladder 174 supported upon a hardened plastic end plug 175. In combination, a secondary end joint defining bladder 176 exhibits an external lubricant plastic face 178 for contacting an opposing bone end-defining surface (not shown). An inner hardened plastic insert 180 is inserted lengthwise within the existing bone 172, prior to injection and formation of the curable fluidic/gelatinous combination, and in order to fill in and strengthen such as an atrophying bone cavity. As further shown in FIG. 13A, a cutaway view taken along line 13A-13A of FIG. 13 illustrates the concentric arrangement of the inner plastic support 180, injected liquid plastic bladder 174, and outer bone 172 and outer plug layer 175.

Having described my invention, other and additional preferred embodiments will become apparent to those skilled in the art to which it pertains, without deviating from the scope of the appended claims.

I claim:

1. An artificial joint configured for implantation between a first bone and a second bone, each of the bones defining a contoured and opposing end face which collectively define a joint location, the artificial joint comprising:

a plurality of movable elements sized to be supported between the end faces and permitting multi-directional motion of the artificial joint, the plurality of movable elements comprising at least three disks that are concentrically stacked and inter-movable, wherein each preceding disk comprises an underside projecting tab sitting within a channel defined along a top surface of a respective succeeding disk in order to establish a range of limited eccentric motion of each preceding disk across the to surface of each respective succeeding disk, wherein each succeeding disk has a diameter greater than a respective preceding disk.

2. The artificial joint as described in claim 1, the bones each being constructed from at least one of a plasticized and a metallic material.

3. The artificial joint as described in claim 2, each of the bones exhibiting a specified shape and size and collectively establishing a joint location selected from a group including at least one of a knee joint location and a ball and socket joint location.

4. The artificial joint as described in claim 1, wherein the to surface of each disk is flat, and wherein a plurality of radially directed and lubricating passageways are defined across each of the top surfaces.

5. An artificial implant, comprising:
a pair of three dimensional and structurally extending artificial bones, each defining a contoured and opposing end face which is encased with a plasticized material, and which collectively define therebetween a joint location; and
at least three inter-movable and concentrically stacked disks supported between the end faces and permitting multi-directional motion between the artificial bones, wherein each preceding disk comprises an underside projecting tab sitting within a channel defined along a top surface of a respective succeeding disk in order to establish a range of limited eccentric motion of each preceding disk across the to surface of each respective succeeding disk, wherein each succeeding disk has a diameter greater than a respective preceding disk.

6. The artificial implant as described in claim 5, wherein the to surface of each disk is flat, and wherein a plurality of radially directed and lubricating passageways are defined across each of the top surfaces.

7. The artificial implant as described in claim 5, the bone end faces further comprising an inner ball and an outer socket, the disks being arranged in a generally arcuate pattern between the ball and the socket.

8. An artificial joint configured for implantation between a first bone and a second bone, each of the bones defining a contoured and opposing end face which collectively define a joint location, the artificial joint comprising:
a plurality of movable elements sized to be supported between the end faces and permitting multi-directional motion of the artificial joint, the movable elements comprising at least three disks that are concentrically stacked and inter-movable, each of the disks having a flat top surface, wherein a plurality of radially directed and lubricating passageways are defined along each of the top surfaces, wherein the length of each lubricating passageway is equal to the diameter of the disk in which it is defined, wherein each succeeding disk has a diameter greater than a respective preceding disk, and wherein each preceding disk is limitedly and eccentrically movable along the to of surface each succeeding disk.

9. The artificial joint as described in claim 8, each preceding disk further comprising an underside projecting tab sitting within a channel defined across the to surface of each succeeding disk in order to establish a range of limited eccentric motion.

10. The artificial joint as described in claim 8, further comprising the disks establishing a range of controlled eccentric motion between the joint location defining bones.

11. The artificial joint as described in claim 8, further comprising the disks each rotating in either of a first or a second direction.

12. An artificial implant, comprising
a pair of three dimensional and structurally extending artificial bones, each defining a contoured and opposing end face which is encased with a plasticized material, and which collectively define therebetween a joint location; and
at least three inter-movable and concentrically stacked disks supported between the end faces and permitting multi-directional motion between the artificial bones, wherein each of the disks has a flat top surface, wherein a plurality of radially directed and lubricating passageways are defined along each of the top surfaces, wherein the length of each lubricating passageway is equal to the diameter of the disk in which it is defined, wherein each succeeding disk has a diameter greater than a respective preceding disk, and wherein each preceding disk is eccentrically movable along the to of surface each succeeding disk.

13. The artificial implant as described in claim 12, each preceding disk further comprising an underside projecting tab sitting within a channel defined across the top surface of each succeeding disk in order to establish a range of limited eccentric motion of the artificial implant.

* * * * *

UNITED STATES PATENT AND TRADEMARK OFFICE
CERTIFICATE OF CORRECTION

| | | |
|---|---|---|
| PATENT NO. | : 7,972,380 B2 | Page 1 of 1 |
| APPLICATION NO. | : 12/212161 | |
| DATED | : July 5, 2011 | |
| INVENTOR(S) | : Miguel A. Linares | |

It is certified that error appears in the above-identified patent and that said Letters Patent is hereby corrected as shown below:

Column 9, Line 35 – Replace "to" with --top--.

Signed and Sealed this

Twentieth Day of December, 2011

David J. Kappos
*Director of the United States Patent and Trademark Office*